United States Patent
Frerot et al.

(10) Patent No.: US 11,690,390 B2
(45) Date of Patent: *Jul. 4, 2023

(54) TASTE MODIFYING PRODUCT

(71) Applicant: Firmenich SA, Satigny (CH)

(72) Inventors: Eric Frerot, Satigny (CH); Kasia Aeberhardt, Satigny (CH)

(73) Assignee: Firmenich SA, Satigny (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/690,056

(22) Filed: Mar. 9, 2022

(65) Prior Publication Data

US 2022/0264923 A1 Aug. 25, 2022

Related U.S. Application Data

(63) Continuation of application No. 15/647,934, filed on Jul. 12, 2017, now Pat. No. 11,291,231, which is a continuation of application No. 14/125,721, filed as application No. PCT/EP2012/060641 on Jun. 6, 2012, now abandoned.

(30) Foreign Application Priority Data

Jun. 30, 2011 (EP) .................................. 11172035
Jan. 16, 2012 (EP) .................................. 12151273

(51) Int. Cl.
| | |
|---|---|
| A23L 27/20 | (2016.01) |
| A23L 27/00 | (2016.01) |
| C07C 235/34 | (2006.01) |
| C07D 317/60 | (2006.01) |

(52) U.S. Cl.
CPC ......... *A23L 27/204* (2016.08); *A23L 27/2052* (2016.08); *A23L 27/88* (2016.08); *C07C 235/34* (2013.01); *C07D 317/60* (2013.01)

(58) Field of Classification Search
CPC .... A23L 27/204; A23L 27/2052; A23L 27/88; C07C 235/34; C07C 233/11; C07D 317/60

See application file for complete search history.

*Primary Examiner* — Nikki H. Dees
(74) *Attorney, Agent, or Firm* — Robert S. Dailey

(57) ABSTRACT

The present invention relates to the use of a compound according to formula (I)

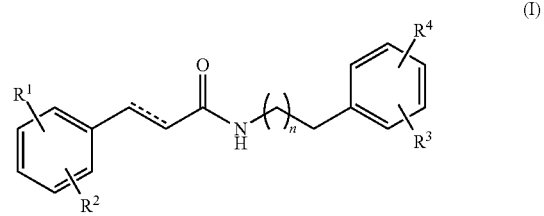

in the form of any one of its stereoisomers or a mixture thereof, and wherein n is an integer from 0 to 2;
the dotted line represents a carbon-carbon single or double bond; and
each of $R^1$ to $R^4$, when taken independently from each other, represents a hydrogen atom or represents a $R^5$ or $OR^5$ group, $R^5$ representing a $C_1$ to $C_5$, or even a $C_1$ to $C_5$, alkyl group; and optionally one of the groups $R_1$ to $R_4$ represents —OH; and/or
when $R_1$ and $R_2$ are taken together, and/or $R_3$ and $R_4$ are taken together, represent a $OCH_2O$ group, provided said groups taken together are adjacent substituents of the phenyl group;
as an ingredient to confer, enhance, improve or modify the kokumi or umami taste of a flavored article.

9 Claims, No Drawings

TASTE MODIFYING PRODUCT

CROSS REFERENCE TO RELATED APPLICATIONS

The present application is a continuation of U.S. patent application Ser. No. 15/647,934, filed Jul. 12, 2017, which is a continuation of U.S. patent application Ser. No. 14/125,721, filed Dec. 12, 2013, which is the U.S. national stage application of PCT Application No. PCT/EP2012/060641, filed Jun. 6, 2012, which claims priority to European Patent Application No. 11172035.5, filed Jun. 30, 2011, and European Patent Application No. 12151273.5, filed Jan. 16, 2012. Each of these applications is hereby incorporated by reference in its entirety.

TECHNICAL FIELD

The present invention relates to the field of taste. More particularly, it concerns the use of certain cinnamic acid derived amides as taste-enhancing ingredients to impart or reinforce the tastes known as kokumi or umami.

The present invention also concerns compositions or articles containing at least one of the aforementioned compounds.

BACKGROUND AND PRIOR ART

Various cinnamic acid derived amides are known to naturally occur in plants such as *Zanthoxylum rubescens* (Rutaceae) [Amides from *Zanthoxylum Rubescens*. Adesina, S. K.; Reisch, J. *Phytochem.* 1989, 3, 839-842.] or *Piperaceae* [Chemical constituents of peppers (*Piper* spp.) and application to food preservation: naturally occurring antioxidative compounds. Nakatani, N.; Inatani, R.; Ohta, H.; Nishioka, A., *Environ. Health Perspectives* 1986, 67, 135-142].

Since vanilloid amides, such as capsaicin or piperine are usually found in pepper or capsicum species, they generally have a pungent or hot taste. It would be desirable to avoid this. US2003/0152682 (Bayer Polymers LLC) and EP 1 323 356 (Symrise) disclose the use of ferullic acid amides as pungent compounds or heat generating-system for oral hygiene products. Included in this document is the compound trans-rubenamine, but it is not described or even suggested to have an umami taste. EP 2 138 152 (to Henkel) describes mouthwash compositions containing ferrulic acid derived amides among other amides or pungent, or cooling compounds. However, none of these documents anticipate, report or suggest that the compounds described therein have organoleptic properties that can be used to impart or reinforce a kokumi or umami taste.

In New Developments in Umami (Enhancing) Molecules, Winkel et al, Chemistry & Biodiversity, Vol 5 (2008), p1195-1203, a review of known umami modifying compounds is given. However, there is no suggestion of the compounds of the present invention.

Kokumi and umami are now established descriptors in the field of taste and are known to supplement, enhance, or modify the taste and/or aroma of a food without necessarily having a strong characteristic taste or aroma of their own. A desire for kokumi and umami exists for a wide range of foods like soups, sauces, savory snacks, prepared meals, condiments, etc. Moreover, they are often found to complement or enhance foodstuffs which have a savory or salty characteristic and, as a result, may be useful where sodium or salt reduction is desired.

Umami is one of the five basic tastes sensed by specialized receptor cells present on the human tongue. Umami applies to the sensation of savoriness, and particularly to the detection of glutamates and/or ribotides which are common in meats, cheese and other protein-rich foods. The behavior of umami receptors explains why foods containing monosodium glutamate (MSG) often taste "fuller". However, some consumers are apparently sensitive to MSG and may suffer from headaches or other illnesses upon consuming it. Thus replacement of MSG, at least partially, can be desirable.

Kokumi has been described variously as "deliciousness", "continuity", "mouthfulness", "mouthfeel" and "thickness". It exists naturally in a variety of foods such as cheese, giving a 'mature' cheese taste; vegetable flavors, particularly tomato; meat, where it gives a fullness and longer lasting taste; mayonnaise & dressings, where it can round out acid notes; fat-reduced food products, where it gives a similar fullness to full-fat products; herbs and spice; and soups, especially miso soup.

US2006/057268 reports saturated or unsaturated N-alkamide and their use as umami ingredients.

It would be desirable to provide a flavor or taste enhancing ingredient that has umami or kokumi characteristics. It would be even more desirable to provide a flavor or taste enhancing ingredient that has umami and kokumi characteristics.

DESCRIPTION OF THE INVENTION

We have now surprisingly discovered that a certain class of cinnamic acid derived amide derivatives can be used as flavor or taste enhancing ingredients, for instance to impart or reinforce the kokumi or umami taste of a flavoring composition or of a flavored food.

Accordingly, the present invention provides the use of a compound of formula

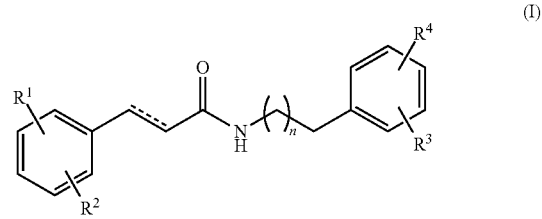

(I)

in the form of any one of its stereoisomers or a mixture thereof, and wherein n is an integer from 0 to 2;

the dotted line represents a carbon-carbon single or double bond; and each of $R^1$ to $R^4$, when taken independently from each other, represents a hydrogen atom or represents a $R^5$ or $OR^5$ group, $R^5$ representing a $C_1$ to $C_5$, or even a $C_1$ to $C_3$, alkyl group; and optionally one of the groups $R_1$ to $R_4$ represents —OH; and/or when $R_1$ and $R_2$ are taken together, and/or $R_3$ and $R_4$ are taken together, represent a $OCH_2O$ group, provided said groups taken together are adjacent substituents of the phenyl group;

as an ingredient to confer, enhance, improve or modify the kokumi or umami taste of a flavored article.

For the sake of clarity, by the expression "any one of its stereoisomers", or the similar, it is meant the normal meaning understood by a person skilled in the art, i.e. that the invention's compound can be a pure enantiomer (if chiral) or diastereomer (e.g. the double bond is in a conformation E or Z).

For the sake of clarity, by the expression "wherein the dotted line represents carbon-carbon single or double bond", or the similar, it is meant the normal meaning understood by a person skilled in the art, i.e. that the whole bonding (solid and dotted line) between the carbon atoms connected by said dotted line is a carbon-carbon single or double bond.

One advantage of the present invention is that the compounds confer umami and/or kokumi taste to a product without detrimentally affecting the flavor profile of the product.

According to a particular embodiment of the invention, said compound (I) is selected from the group of compounds in which
n is 0 or 1;
the dotted line represents carbon-carbon single or double bond; and each of $R^1$ to $R^4$, taken independently from each other, represents a hydrogen atom or represents a $R^5$ or $OR^5$ group, $R^5$ representing a $C_1$ to $C_5$, or even a $C_1$ to $C_3$, alkyl group.

According to a particular embodiment of the invention, said compound (I) is selected from the group of compounds in which $R_1$ and $R_2$ both represent methoxy groups and n is 1.

According to any one of the above embodiments of the invention, said dotted line represents a carbon-carbon double bond.

According to a particular embodiment of the invention, said compound (I) is a compound of formula

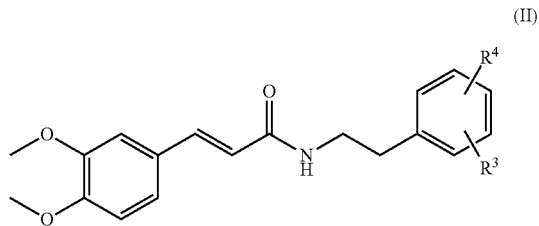

(II)

in the form of any one of its stereoisomers or a mixture thereof, and wherein each of $R^3$ or $R^4$, taken independently from each other, represents a hydrogen atom or represents a $R^5$ or $OR^5$ group, $R^5$ representing a $C_1$ to $C_5$, or even a $C_1$ to $C_3$ alkyl group.

According to any one of the above embodiments of the invention, $R^3$ represents a hydrogen atom or represents a $R^5$ or $OR^5$ group, and $R^4$ represents a $R^5$ or $OR^5$ group, $R^5$ representing a $C_1$ to $C_5$, or even a $C_1$ to $C_3$, alkyl group.

According to any one of the above embodiments of the invention, $R^3$ represents a hydrogen atom or represents a $R^5$ group, and $R^4$ represents a $R^5$ or $OR^5$ group, $R^5$ representing a $C_1$ to $C_5$, or even a $C_1$ to $C_3$, alkyl group.

According to any one of the above embodiments of the invention, $R^3$ represents a hydrogen atom or represents a $R^5$ group, and $R^4$ represents a $R^5$, $R^5$ representing a $C_1$ to $C_5$, or even a $C_1$ to $C_3$, alkyl group.

According to any one of the above embodiments of the invention, $R^5$ represents a methyl, ethyl, propyl or iso-propyl group.

The compounds of formula (II) wherein:
$R^3$ represents a hydrogen atom or represents a $C_1$ to $C_5$, or even a $C_{1-3}$, alkyl group or a $OR^6$ group, $R^6$ representing a $C_1$ to $C_5$, or even a $C_{2-3}$, alkyl group; and $R^4$ represents a $C_1$ to $C_5$, or even a $C_{1-3}$, alkyl group or a $OR^6$ group, $R^6$ representing a $C_1$ to $C_5$, or even a $C_{1-3}$, alkyl group;
are also novel compounds and therefore they represent another aspect of the invention.

According to any one of the above embodiments of the invention, said novel compounds are those wherein $R^3$ represents a hydrogen atom or a $C_{1-3}$, alkyl group and $R^4$ represents a $C_{1-3}$, alkyl group or $OR^6$ group, $R^6$ representing a $C_1$ to $C_3$ alkyl group.

According to any one of the above embodiments of the invention, said compound (I) or (II) is a $C_{19-25}$ compound, or even a $C_{19-22}$ compound.

According to any one of the above embodiments of the invention, the non-aromatic carbon-carbon double bond of compound (I) or (II) can be in a configuration Z or E or a mixture thereof. According to any one of the above embodiments of the invention, said compound (I) or (II) is in the form of a mixture of the E and Z stereoisomers, said mixture comprising at least 50% w/w, or at least 80% w/w, of the stereoisomer E, the remaining being essentially the Z stereoisomer.

According to a particular aspect of the present invention, said compound (I) is selected amongst (E)-3-(3,4-dimethoxyphenyl)-N-(4-methoxyphenethyl)acrylamide (referenced in the Examples as Amide 1), (E)-3-(3,4-dimethoxyphenyl)-N-(3-methoxyphenethyl)acrylamide (referenced in the Examples as Amide 4), (E)-3-(3,4-dimethoxyphenyl)-N-(3-ethoxyphenethyl)acrylamide (referenced in the Examples as Amide 7), (E)-3-(3,4-dimethoxyphenyl)-N-(3-propoxyphenethyl)acrylamide (referenced in the Examples as Amide 8), (E)-3-(3,4-dimethoxyphenyl)-N-(4-isopropoxy-phenethyl)acrylamide (referenced in the Examples as Amide 9), (E)-3-(3,4-dimethoxyphenyl)-N-(4-ethylphenethyl)acrylamide (referenced in the Examples as Amide 10), (E)-3-(3,4-dimethoxyphenyl)-N-(3,4-dimethylphenethyl)acrylamide (referenced in the Examples as Amide 11), (E)-3-(3,4-dimethoxyphenyl)-N-(4-isopropylphenethyl)acrylamide (referenced in the Examples as Amide 12) or (E)-3-(3,4-dimethoxyphenyl)-N-(3-methylphenethyl)acrylamide (referenced in the Examples as Amide 17).

The compounds of the invention can be used alone or in mixtures and provide a strong kokumi or umami taste at exceptionally low levels.

As mentioned above, the invention concerns the use of a compound of formula (I) as a taste-conferring or enhancing ingredient, and in particular to impart or reinforce kokumi or umami taste.

According to a particular embodiment of the invention, said compound (I) is used to impart or reinforce kokumi or umami taste as well as to enhance the saltiness and/or savory perception of a flavor.

According to a particular embodiment of the invention, such use is very much appreciated by flavorists to impart or enhance the kokumi or umami taste in savory flavors, such as beef, chicken, pork, and seafood. Surprisingly, in seafood applications such as surimi, or seafood bouillons or snack flavors, compounds according to formula (I) are also found to enhance the perception of sweetness and longevity of the flavor. By contrast, in beef flavors, the compounds according to formula (I) are found to enhance perception of fattiness and tallow notes. Additionally we found that said compounds can increase juiciness in meat based products.

In other words the present invention concerns a method to confer, enhance, improve or modify the taste properties, as indicated above, of a flavoring composition or of a flavored article, which method comprises adding to said composition or article an effective amount of at least a compound of formula (I). In the context of the present invention "use of a compound of formula (I)" includes the use of any composition containing compound (I) and which can be advantageously employed in the flavor industry as active ingredient.

In another aspect, the invention provides a taste-modifying composition comprising:
i) as a taste-conferring or modifying ingredient, at least one compound according to formula (I) above;
ii) at least one ingredient selected from the group consisting of a flavor carrier and a flavor base; and
iii) optionally at least one flavor adjuvant.

By "flavor carrier" we mean here a material which is substantially neutral from a flavor point of view, insofar as it does not significantly alter the organoleptic properties of flavoring ingredients. The carrier may be a liquid or a solid.

Suitable liquid carriers include, for instance, an emulsifying system, i.e. a solvent and a surfactant system, or a solvent commonly used in flavors. A detailed description of the nature and type of solvents commonly used in flavor cannot be exhaustive. Suitable solvents include, for instance, propylene glycol, triacetine, triethyl citrate, benzylic alcohol, ethanol, vegetable oils or terpenes.

Suitable solid carriers include, for instance, absorbing gums or polymers, or even encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. Encapsulation is a well known process to a person skilled in the art, and may be performed, for instance, using techniques such as spray-drying, agglomeration, extrusion, coacervation and the like.

By "flavor base" we mean here a composition comprising at least one flavoring ingredient.

Said flavoring ingredient is not a compound of formula (I). Moreover, by "flavoring ingredient" it is meant here a compound, which is used in flavoring preparations or compositions to impart a hedonic effect. In other words such an ingredient, to be considered as being a flavoring one, must be recognized by a person skilled in the art as being able to impart or modify in a positive or pleasant way the taste of a composition, and not just as having a taste.

The nature and type of the flavoring co-ingredients present in the base do not warrant a more detailed description here, the skilled person being able to select them on the basis of its general knowledge and according to intended use or application and the desired organoleptic effect. In general terms, these flavoring co-ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of flavor. It is also understood that said co-ingredients may also be compounds known to release in a controlled manner various types of flavoring compounds.

According to a particular embodiment of the invention, said flavor base comprises another umami imparting flavor ingredient, such as MSG (mono sodium glutamate), and ribotides (a blend, e.g. 50-50 w/w, of IMP (inosine monophosphate) and GMP (guanosine monophosphate)), for example in a MSG/ribotides w/w ratio from 95/5 to 90/10. Or ingredients rich in those compounds mentioned before that are well known to the people skilled in the art.

By "flavor adjuvant" we mean here an ingredient capable of imparting additional added benefit such as a color, a particular light resistance, chemical stability, and so on. A detailed description of the nature and type of adjuvant commonly used in flavoring bases cannot be exhaustive. Nevertheless, such adjuvants are well known to a person skilled in the art, but it has to be mentioned that said ingredients are well known to a person skilled in the art.

A composition consisting of at least one compound of formula (I) and at least one flavor carrier represents a particular embodiment of the invention as well as a flavoring composition comprising at least one compound of formula (I), at least one flavor carrier, at least one flavor base, and optionally at least one flavor adjuvant.

In a highly preferred embodiment, more than one compound of formula (I) is used in combination since it is found that a synergistic enhancement of the kokumi or umami taste can be achieved in this way. Moreover, it is found that the combination of ingredients can provide the desired kokumi or umami taste without imparting undesirable flavor notes.

Moreover, a compound of formula (I) can be advantageously incorporated into flavored articles to positively impart, or modify, the kokumi or umami taste of said articles. Thus, in yet another aspect, the present invention provides a flavored article comprising:
i) as taste-conferring or modifying ingredient, at least one compound of formula (I), as defined above, optionally present as part of a flavoring composition; and
ii) a foodstuff base.

Suitable foodstuff bases, e.g. foods or beverages, can be fried or not, as well as frozen or not, low fat or not, marinated, battered, chilled, dehydrated, instant, canned, reconstituted, retorted or preserved. Typical examples of said foodstuff bases include:
a seasonings or condiment, such as a stock, a savory cube, a powder mix, a flavored oil, a sauce (e.g. a relish, barbecue sauce, a dressing, a gravy or a sweet and/or sour sauce), a salad dressing or a mayonnaise;
a meat-based product, such as a poultry, beef or pork based product, a seafood, surimi, or a fish sausage;
a soup, such as a clear soup, a cream soup, a chicken or beef soup or a tomato or asparagus soup;
a carbohydrate-based product, such as instant noodles, rice, pasta, potatoes flakes or fried, noodles, pizza, tortillas, wraps;
a dairy or fat product, such as a spread, a cheese, or regular or low fat margarine, a butter/margarine blend, a butter, a peanut butter, a shortening, a processed or flavored cheese;
a savory product, such as a snack, a biscuit (e.g. chips or crisps) or an egg product, a potato/tortilla chip, a microwave popcorn, nuts, a bretzel, a rice cake, a rice cracker, etc;
an imitation products, such as a dairy (e.g a reformed cheese made from oils, fats and thickeners) or seafood or meat (e.g. a vegetarian meat replacer, veggie burgers) analogue; or
a pet or animal food.

Particularly preferred foodstuffs in which the compound according to formula (I) finds utility include those having topnotes such as seafood, beef, chicken, vegetables, cheese, fat, tallow and/or marrow are important.

For the sake of clarity, it has to be mentioned that, by "foodstuff" we mean here an edible product, e.g. a food or a beverage. Therefore, a flavored article according to the invention comprises one or more compounds according to formula (I), as well as optional benefit agents, corresponding to taste and flavor profile of the desired edible product, e.g. a savory cube.

The nature and type of the constituents of the foodstuffs or beverages do not warrant a more detailed description here, the skilled person being able to select them on the basis of his general knowledge and according to the nature of said product.

According to any one of the above embodiments of the invention, the taste-modifying composition and the flavored article according to the invention comprise as taste conferring or modifying ingredient a compound of formula (II) wherein $R^3$ represents a hydrogen atom or represents a $R^5$ group, and $R^4$ represents a $R^5$ or $OR^5$ group, $R^5$ representing a $C_1$ to $C_3$ alkyl group. According to any one of the above embodiments of the invention, $R^5$ represents a methyl, ethyl, propyl or iso-propyl group.

The proportions in which the compounds according to the invention can be incorporated into the various aforementioned articles or compositions vary within a wide range of values. These values are dependent on the nature of the article to be flavored and on the desired organoleptic effect as well as the nature of the co-ingredients in a given base when the compounds according to the invention are mixed with flavoring co-ingredients, solvents or additives commonly used in the art.

In the case of flavoring compositions, typical concentrations are in the order of 0.05% to 30%, more preferably 0.1% to 20%, most preferably 0.1% to 10%, of the compounds of the invention based on the weight of the flavoring compositions into which they are incorporated. Concentrations lower than these, such as in the order of 0.5 ppm to 300 ppm by weight, more preferably 5 ppm to 75 ppm, most preferably 8 to 50 ppm, can be used when these compounds are incorporated into flavored articles, the percentage being relative to the weight of the article.

At these levels the taste is typically described as umami-like, lasting, sweet and lingering.

EXAMPLES

The invention will now be described in further detail by way of the following example, wherein the abbreviations have the usual meaning in the art, the NMR spectral data were recorded in CDCl$_3$, with a 400 MHz machine for $^1$H, and a 100 or 125 MHz machine for $^{13}$C, the chemical displacements, δ, are indicated in ppm with respect to TMS as standard, and the coupling constants, J, are expressed in Hz.

Example 1

Preparation of Compound According to the Invention

Synthesis of Amides with Ethyl Chloroformate, General Procedure:

The acid (E)-3-(3,4-dimethoxyphenyl)acrylic acid (typically 33 mmol) and DIEA (diisopropyl ethyl amine, 2 equiv.) were diluted in 200 mL of EtOAc and 50 mL of dichloromethane. The solution was cooled to 15° C. and ethyl chloroformate (1 molar equiv.) was added drop wise. The reaction was stirred for 1 hour before the starting amine (1 molar equiv., diluted 2-3 times in EtOAc) was added. The reaction was stirred overnight at room temperature. It was washed with aqueous 5% KHSO$_4$, brine, aqueous 5% NaHCO$_3$, brine, and then dried over Na$_2$SO$_4$ and evaporated under high vacuum for 3 hours. The crude product was purified by flash chromatography (silica gel; cyclohexane/EtOAc, 2:8) or by recrystallization from EtOAc. Yields were between 50 and 80% on the purified product.

Amide 1:

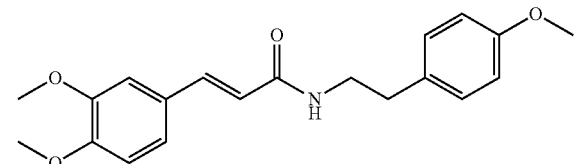

(E)-3-(3,4-dimethoxyphenyl)-N-(4-methoxyphenethyl)acrylamide
Chemical Formula: C$_{20}$H$_{23}$NO$_4$ starting amine: 2-(4-methoxyphenyl)ethanamine
$^1$H NMR: 2.82 (t, J=7.0, 2H), 3.61 (~q, J=7.0, 5.9, 2H), 3.78 (s, 3H), 3.86 (s, 3H), 3.88 (s, 3H), 5.87 (t, J=5.9, 1H), 6.24 (d, J=15.5, 1H), 6.81 (d, J=8.3, 1H), 6.84 (d, J=8.6, 2H), 6.98 (d, J=2.0, 1H), 7.05 (dd, J=8.3, 2.0, 1H), 7.13 (d, J=8.6, 2H), 7.55 (d, J=15.5, 1H).
$^{13}$C NMR: 34.8 (t), 41.0 (t), 55.2 (q), 55.8 (q), 55.9 (q), 109.7 (d), 111.1 (d), 114.1 (d), 118.6 (d), 121.9 (d), 127.8 (s), 129.7 (d), 130.9 (s), 140.7 (d), 149.1 (s), 150.5 (s), 158.3 (s), 166.2 (s).

Amide 2:

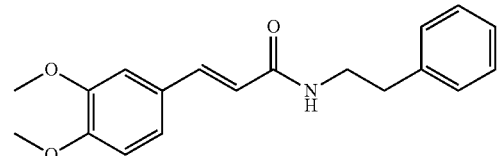

(E)-3-(3,4-dimethoxyphenyl)-N-phenethylacrylamide
Chemical Formula: C$_{19}$H$_{21}$NO$_3$ starting amine: 2-phenylethanamine
$^1$H NMR: 2.89 (t, J=6.8, 2H), 3.66 (~q, J=6.8, 5.5, 2H), 3.87 (s, 3H), 3.89 (s, 3H), 5.72 (t, J=5.5, 1H), 6.21 (d, J=15.5, 1H), 6.83 (d, J=8.3, 1H), 6.99 (d, J=2.0, 1H), 7.06 (dd, J=8.3, 2.0, 1H), 7.20-7.26 (m, 3H), 7.30-7.34 (m, 2H), 7.56. (d, J=15.5, 1H).
$^{13}$C NMR: 35.7 (t), 40.8 (t), 55.9 (q), 55.9 (q), 109.7 (d), 111.1 (d), 118.5 (d), 121.9 (d), 126.5 (d), 127.8 (s), 128.7 (d), 128.8 (d), 139.0 (s), 140.9 (d), 149.1 (s), 150.6 (s), 166.1 (s).

Amide 3:

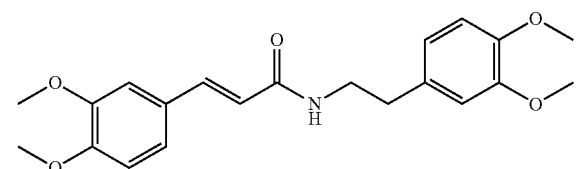

(E)-N-(3,4-dimethoxyphenethyl)-3-(3,4-dimethoxyphenyl)acrylamide
Chemical Formula: C$_{21}$H$_{25}$NO$_5$ starting amine: 2-(3,4-dimethoxyphenyl)ethanamine ¹H NMR: 2.84 (t, J=6.9, 2H), 3.63 (~q, J=6.9, 6.0, 2H), 3.86 (s, 6H), 3.87 (s, 3H), 3.89 (s, 3H), 5.79 (t, J=6.0, 1H), 6.23 (d, J=15.5, 1H), 6.75 (~d, J=8.0, 1H), 6.77 (d, J=2.0, 1H), 6.81 (d, J=8.0, 1H), 6.83 (d, J=8.0, 1H), 6.99 (d, J=2.0, 1H), 7.06 (dd, J=8.3, 2.0, 1H), 7.56 (d, J=15.5, 1H).

¹³C NMR: 35.2 (t), 40.9 (t), 55.86 (q), 55.88 (q), 55.93 (2 q), 109.6 (d), 111.1 (d), 111.4 (d), 112.0 (d), 118.5 (d), 120.7 (d), 122.0 (d), 127.8 (s), 131.4 (s), 140.9 (d), 147.7 (s), 149.1 (s), 149.1 (s), 150.6 (s), 166.1 (s);

Amide 4:

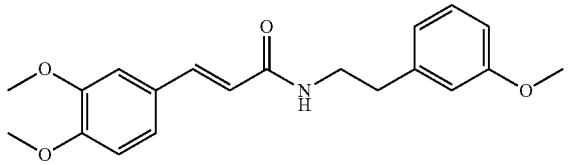

(E)-3-(3,4-dimethoxyphenyl)-N-(3-methoxyphenethyl)acrylamide
Chemical Formula: $C_{20}H_{23}NO_4$ starting amine: 2-(3-methoxyphenyl)ethanamine ¹H NMR: 2.86 (t, J=6.9, 2H), 3.65 J=7.0, 5.7, 2H), 3.79 (s, 3H), 3.87 (s, 3H), 3.89 (s, 3H), 5.76 (t, J=5.7, 1H), 6.22 (d, J=15.5, 1H), 6.76-6.82 (m, 3H), 6.83 (d, J=8.4, 1H), 6.99 (d, J=2.0, 1H), 7.05 (dd, J=8.4, 2.0, 1H), 7.23 (dt, J=7.5, 1.0, 1H), 7.56 (d, J=15.5, 1H).

¹³C NMR: 35.7 (t), 40.6 (t), 55.2 (q), 55.8 (q), 55.9 (q), 109.7 (d), 111.1 (d), 111.9 (d), 114.5 (d), 118.6 (d), 121.1 (d), 121.9 (d), 127.8 (s), 129.7 (d), 140.6 (s), 140.8 (d), 149.1 (s), 150.6 (s), 159.8 (s), 166.2 (s).

Amide 5:

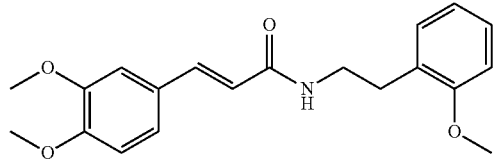

(E)-3-(3,4-dimethoxyphenyl)-N-(2-methoxyphenethyl)acrylamide
Chemical Formula: $C_{20}H_{23}NO_4$ starting amine: 2-(2-methoxyphenyl)ethanamine ¹H NMR: 2.90 (t, J=6.8, 2H), 3.62 (~q, J=6.8, 5.6, 2H), 3.84 (s, 3H), 3.87 (s, 3H), 3.88 (s, 3H), 5.91 (t, J=5.6, 1H), 6.22 (d, J=15.5, 1H), 6.82 (d, J=8.3, 1H), 6.87 (~dd, J=8.4, 1.0, 1H), 6.91 (dd, J=7.5, 1.0, 1H), 6.99 (d, J=1.9, 1H), 7.05 (dd, J=8.3, 1.9, 1H), 7.15 (dd, J=7.5, 1.8, 1H), 7.22 (dt, J=7.5, 1.8, 1H), 7.53 (d, J=15.5, 1H).

¹³C NMR: 30.3 (t), 39.8 (t), 55.3 (q), 55.8 (q), 55.9 (q), 109.7 (d), 110.4 (d), 111.1 (d), 118.9 (d), 120.7 (d), 121.8 (d), 127.4 (s), 127.9 (d), 127.9 (s), 130.6 (d), 140.4 (d), 149.1 (s), 150.5 (s), 157.6 (s), 166.1 (s).

Amide 6:

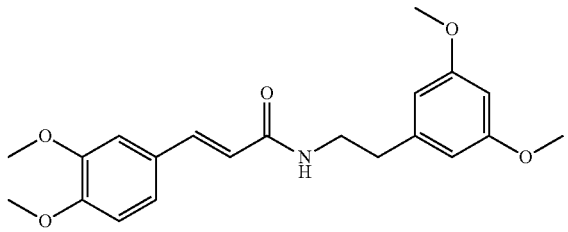

(E)-N-(3,5-dimethoxyphenethyl)-3-(3,4-dimethoxyphenyl)acrylamide
Chemical Formula: $C_{21}H_{25}NO_5$ Starting amine: 2-(3,5-dimethoxyphenyl)ethanamine ¹H NMR: 2.82 (t, J=6.9, 2H), 3.64 (~q, J=6.9, 5.7, 2H), 3.76 (s, 3H), 3.87 (s, 3H), 3.88 (s, 3H), 5.85 (t, J=5.7, 1H), 6.24 (d, J=15.7, 1H), 6.34 (t, J=2.2, 1H), 6.38 (d, J=2.2, 1H), 6.82 (d, J=8.3, 1H), 6.99 (d, J=2.0, 1H), 7.05 (dd, J=8.3, 2.0, 1H), 7.55 (d, J=15.7, 1H).

¹³C NMR: 36.0 (t), 40.5 (t), 55.3 (q), 55.8 (q), 55.9 (q), 98.4 (d), 106.8 (d), 109.7 (d), 111.1 (d), 118.6 (d), 122.0 (d), 127.8 (s), 140.8 (d), 141.3 (s), 149.1 (s), 150.6 (s), 161.0 (s), 166.2 (s).

Amide 7:

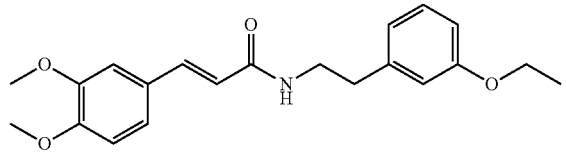

(E)-3-(3,4-dimethoxyphenyl)-N-(3-ethoxyphenethyl)acrylamide
Chemical Formula: $C_{21}H_{25}NO_4$ starting amine: 2-(3-ethoxyphenyl)ethanamine ¹H NMR: 1.40 (t, J=7.0, 3H), 2.85 (t, J=6.9, 2H), 3.65 (~q, J=6.9, 5.6, 2H), 3.88 (s, 3H), 3.89 (s, 3H), 4.02 (q, J=7.0, 2H), 5.70 (t, J=5.6, 1H), 6.21 (d, J=15.4, 1H), 6.76-6.81 (m, 3H), 6.83 (d, J=8.3, 1H), 7.00 (d, J=2.0, 1H), 7.06 (dd, J=8.3, 2.0, 1H), 7.20-7.25 (m, 1H), 7.55 (d, J=15.4, 1H).

¹³C NMR: 14.9 (q), 35.7 (t), 40.6 (t), 55.9 (q), 55.9 (q), 63.4 (t), 109.7 (d), 111.1 (d), 112.4 (d), 115.1 (d), 118.6 (d), 121.0 (d), 122.0 (d), 127.8 (s), 129.7 (d), 140.5 (s), 140.8 (d), 149.1 (s), 150.6 (s), 159.2 (s), 166.1 (s).

Amide 8:

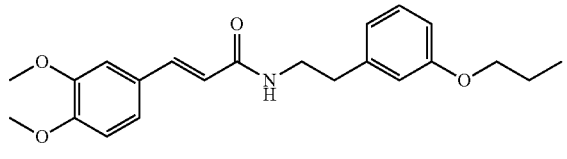

(E)-3-(3,4-dimethoxyphenyl)-N-(3-propoxyphenethyl)acrylamide
Chemical Formula: $C_{22}H_{27}NO_4$ starting amine: 2-(3-propoxyphenyl)ethanamine ¹H NMR: 1.01 (t, J=7.4, 3H), 1.79 (~hex, J=7.4, 6.5, 2H), 2.85 (t, J=6.9, 2H), 3.65 (~q, J=6.9, 5.7, 2H), 3.87 (s, 3H), 3.88 (s, 3H), 3.90 (t, J=6.5, 2H), 5.70 (t, J=5.7, 1H), 6.22 (d, J=15.5, 1H), 6.76-6.81 (m, 3H), 6.82 (d, J=8.4, 1H), 6.99 (d, J=1.9, 1H), 7.05 (dd, J=8.4, 2.0, 1H), 7.19-7.23 (m, 1H), 7.55 (d, J=15.4, 1H).

$^{13}$C NMR: 10.5 (q), 22.6 (t), 35.7 (t), 40.6 (t), 55.8 (q), 55.9 (q), 69.5 (t), 109.7 (d), 111.1 (d), 112.5 (d), 115.1 (d), 118.6 (d), 120.9 (d), 122.0 (d), 127.8 (s), 129.6 (d), 140.5 (s), 140.8 (d), 149.1 (s), 150.6 (s), 159.4 (s), 166.1 (s).

Amide 9:

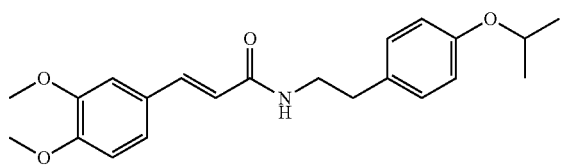

(E)-3-(3,4-dimethoxyphenyl)-N-(4-isopropoxyphenethyl)acrylamide
Chemical Formula: $C_{22}H_{27}NO_4$ starting amine: 2-(4-isopropoxyphenyl)ethanamine $^1$H NMR: 1.32 (d, J=6.1, 6H), 2.81 (t, J=6.9, 2H), 3.61 (~q, J=6.9, 5.8, 2H), 3.87 (s, 3H), 3.88 (s, 3H), 4.51 (hept, J=6.1, 1H), 5.80 (t, J=5.8, 1H), 6.23 (d, J=15.5, 1H), 6.81-6.85 (m, 3H), 6.99 (d, J=2.0, 1H), 7.05 (dd, J=8.4, 2.0, 1H), 7.11 (~d, J=8.6, 2H), 7.55 (d, J=15.5, 1H).

$^{13}$C NMR: 22.1 (q), 34.8 (t), 40.9 (t), 55.8 (q), 55.9 (q), 69.9 (d), 109.7 (d), 111.1 (d), 116.1 (d), 118.6 (d), 121.9 (d), 127.8 (s), 129.7 (d), 130.7 (d), 140.8 (d), 149.1 (s), 150.5 (s), 156.6 (s), 166.1 (s).

Amide 10:

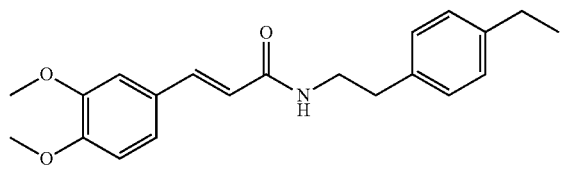

(E)-3-(3,4-dimethoxyphenyl)-N-(4-ethylphenethyl)acrylamide
Chemical Formula: $C_{21}H_{25}NO_3$ starting amine: 2-(4-ethylphenyl)ethanamine $^1$H NMR: 1.23 (t, J=7.6, 3H), 2.63 (q, J=7.6, 2H), 2.85 (t, J=6.8, 2H), 3.64 (~q, J=6.8, 5.6, 2H), 3.87 (s, 3H), 3.89 (s, 3H), 5.73 (t, J=5.6, 1H), 6.22 (d, J=15.6, 1H), 6.81-6.85 (m, 3H), 6.83 (d, J=8.4, 1H), 6.99 (d, J=2.0, 1H), 7.06 (dd, J=8.4, 2.0, 1H), 7.15 (broad s, 4H), 7.55 (d, J=15.6, 1H).

$^{13}$C NMR: 15.6 (q), 28.4 (t), 35.3 (t), 40.8 (t), 55.8 (q), 55.9 (q), 109.7 (d), 111.1 (d), 118.7 (d), 121.9 (d), 127.8 (s), 128.1 (d), 128.7 (d), 136.1 (s), 140.7 (d), 142.4 (s), 149.1 (s), 150.5 (s), 166.1 (s).

Amide 11:

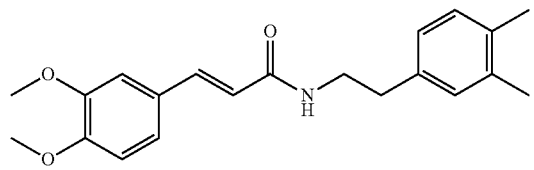

(E)-3-(3,4-dimethoxyphenyl)-N-(3,4-dimethylphenethyl)acrylamide
Chemical Formula: $C_{21}H_{25}NO_3$ starting amine: 2-(3,4-dimethylphenyl)ethanamine
$^1$H NMR: 2.24 (broad s, 6H), 2.82 (t, J=7.1, 2H), 3.63 (~q, J=7.1, 5.5, 2H), 3.87 (s, 3H), 3.88 (s, 3H), 5.75 (t, J=5.5, 1H), 6.22 (d, J=15.6, 1H), 6.82 (d, J=8.4, 1H), 6.95 (dd, J=7.7, 1.8, 1H), 6.98-7.00 (m, 2H), 7.04-7.08 (m, 2H), 7.55 (d, J=15.6, 1H).

$^{13}$C NMR: 19.3 (q), 19.8 (q), 35.2 (t), 40.8 (t), 55.9 (q), 55.9 (q), 109.7 (d), 111.1 (d), 118.6 (d), 121.9 (d), 126.1 (d), 127.9 (s), 129.9 (d), 130.1 (d), 134.7 (s), 136.2 (s), 136.8 (s), 140.7 (d), 149.1 (s), 150.6 (s), 166.1 (s).

Amide 12:

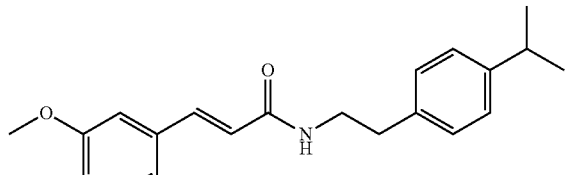

(E)-3-(3,4-dimethoxyphenyl)-N-(4-isopropylphenethyl)acrylamide
Chemical Formula: $C_{22}H_{27}NO_3$ starting amine: 2-(4-isopropylphenyl)ethanamine $^1$H NMR: 1.25 (t, J=7.0, 3H), 2.85 (t, J=6.9, 2H), 2.89 (hept, J=7.0, 1H), 3.65 J=6.9, 5.4, 2H), 3.88 (s, 3H), 3.89 (s, 3H), 5.71 (t, J=5.4, 1H), 6.22 (d, J=15.6, 1H), 6.83 (d, J=8.4, 1H), 7.00 (d, J=2.0, 1H), 7.06 (dd, J=8.4, 2.0, 1H), 7.14-7.19 (m, 4H), 7.56 (d, J=15.6, 1H).

$^{13}$C NMR: 24.0 (q), 33.7 (d), 35.3 (t), 40.8 (t), 55.9 (q), 55.9 (q), 109.7 (d), 111.1 (d), 118.6 (d), 121.9 (d), 126.7 (d), 127.9 (s), 128.7 (d), 136.2 (s), 140.8 (d), 147.1 (s), 149.1 (s), 150.6 (s), 166.1 (s).

Amide 13:

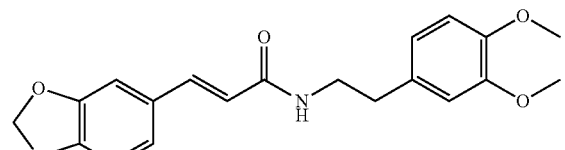

(E)-3-(benzo[d][1,3]dioxol-5-yl)-N-(3,4-dimethoxyphenethyl)acrylamide
Chemical Formula: $C_{20}H_{21}NO_5$ starting amine: 2-(3,4-dimethoxyphenyl)ethanamine starting acid: (E)-3-(benzo[d][1,3]dioxol-5-yl)acrylic acid $^1$H NMR: 2.83 (t, J=7.1, 2H), 3.62 (~q, J=7.1, 5.9, 2H), 3.858 (s, 3H), 3.862 (s, 3H), 5.70 (t, J=5.9, 1H), 5.98 (s, 2H), 6.16 (d, J=15.6, 1H), 6.74-6.83 (m, 4H), 6.96-6.97 (m, 2H), 7.56 (d, J=15.6, 1H).

$^{13}$C NMR: 35.2 (t), 40.9 (t), 55.9 (q), 55.9 (q), 101.4 (t), 106.3 (d), 108.5 (d), 111.4 (d), 112.0 (d), 118.6 (d), 120.7 (d), 123.8 (d), 129.2 (s), 131.4 (s), 140.8 (d), 147.7 (s), 148.2 (s), 149.0 (s), 149.1 (s), 166.0 (s).

Amide 14:

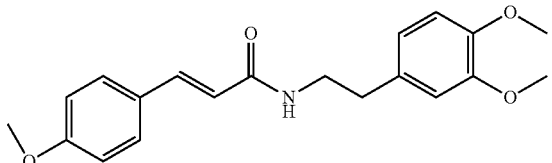

(E)-N-(3,4-dimethoxyphenethyl)-3-(4-methoxyphenyl)acrylamide
Chemical Formula: $C_{20}H_{23}NO_4$ starting amine: 2-(3,4-dimethoxyphenyl)ethanamine
starting acid: (E)-3-(4-methoxyphenyl)acrylic acid $^1$H NMR: 2.83 (t, J=6.9, 2H), 3.62 (~q, J=6.9, 5.7, 2H), 3.80 (s, 3H), 3.83 (s, 3H), 3.84 (s, 3H), 5.97 (t, J=5.7, 1H), 6.25 (d, J=15.6, 1H), 6.73-6.81 (m, 3H), 6.84 (d, J=8.8, 2H), 7.40 (d, J=8.8, 2H), 7.57 (d, J=15.6, 1H).

$^{13}$C NMR: 35.3 (t), 41.0 (t), 55.3 (q), 55.8 (q), 55.9 (q), 111.4 (d), 112.0 (d), 114.2 (d), 118.4 (d), 120.7 (d), 127.5 (s), 129.3 (d), 131.5 (s), 140.5 (d), 147.7 (s), 149.0 (s), 160.8 (s), 166.3 (s).

Amide 15:

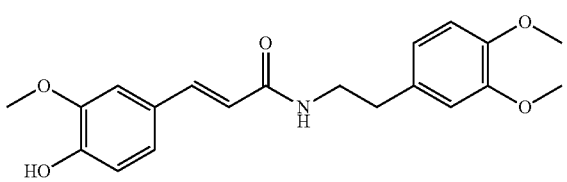

(E)-N-(3,4-dimethoxyphenethyl)-3-(4-hydroxy-3-methoxyphenyl)acrylamide
Chemical Formula: $C_{20}H_{23}NO_5$ starting amine: 2-(3,4-dimethoxyphenyl)ethanamine
starting acid: (E)-3-(4-acetoxy-3-methoxyphenyl)acrylic acid. After the coupling, deprotection step was performed in MeOH/5% aq $Na_2CO_3$ (1:1).

$^1$H NMR: 2.83 (t, J=6.9, 2H), 3.63 (~q, J=6.9, 5.7, 2H), 3.86 (s, 3H), 3.87 (s, 3H), 3.90 (s, 3H), 5.63 (t, J=5.7, 1H), 6.17 (d, J=15.4, 1H), 6.74 (~d, J=1.9, 1H), 6.76 (~dd, J=8.0, 1.9, 1H), 6.82 (d, J=8.0, 1H), 6.89 (d, J=8.0, 1H), 6.96 (d, J=1.9, 1H), 7.03 (dd, J=8.2, 1.9, 1H), 7.52 (d, J=15.4, 1H). Exchangeable OH not seen.

$^{13}$C NMR: 35.2 (t), 40.9 (t), 55.9 (q), 56.0 (q), 109.6 (d), 111.4 (d), 112.0 (d), 114.7 (d), 118.0 (d), 120.7 (d), 122.2 (d), 127.3 (s), 131.4 (s), 141.2 (d), 146.7 (s), 147.4 (s), 147.7 (s), 149.1 (s), 166.3 (s).

Amide 16:

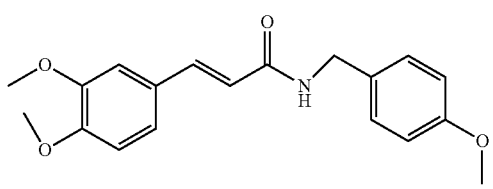

(E)-3-(3,4-dimethoxyphenyl)-N-(4-methoxybenzyl)acrylamide
Chemical Formula: $C_{19}H_{21}NO_4$ starting amine: (4-methoxyphenyl)methanamine
starting acid: (E)-3-(3,4-dimethoxyphenyl)acrylic acid $^1$H NMR: 3.79 (s, 3H), 3.87 (s, 3H), 3.89 (s, 3H), 4.49 (d, J=5.7, 2H), 5.93 (t, J=5.7, 1H), 6.29 (d, J=15.5, 1H), 6.83 (d, J=8.4, 1H), 6.86 (~d, J=8.7, 2H), 7.00 (d, J=2.0, 1H), 7.06 (dd, J=8.4, 2.0, 1H), 7.24 (~d, J=8.7, 2H), 7.59 (d, J=15.5, 1H).

$^{13}$C NMR: 43.3 (t), 55.3 (q), 55.8 (q), 55.9 (q), 109.7 (d), 111.1 (d), 114.1 (d), 118.4 (d), 121.9 (d), 127.8 (s), 129.3 (d), 130.4 (s), 141.1 (d), 149.1 (s), 150.6 (s), 159.1 (s), 165.9 (s).

Amide 17:

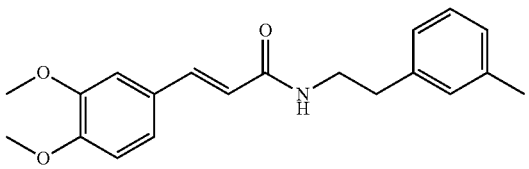

(E)-3-(3,4-dimethoxyphenethyl)-N-(3-methylphenethyl)acrylamide
Chemical Formula: $C_{20}H_{23}NO_3$ starting amine: 2-(3-methylphenyl)ethanamine
starting acid: (E)-3-(3,4-dimethoxyphenyl)acrylic acid $^1$H NMR: 2.34 (s, 3H), 2.85 (t, J=7.1, 2H), 3.65 J=7.1, 5.4, 2H), 3.88 (s, 3H), 3.89 (s, 3H), 5.67 (t, J=5.4, 1H), 6.21 (d, J=15.5, 1H), 6.83 (d, J=8.3, 1H), 7.00 (d, J=2.0, 1H), 7.02-7.07 (m, 4H), 7.21 (~d, J=7.5, 1H), 7.55 (d, J=15.5, 1H).

$^{13}$C NMR: 21.4 (q), 35.6 (t), 40.7 (t), 55.9 (q), 55.9 (q), 109.7 (d), 111.1 (d), 118.6 (d), 121.9 (d), 125.8 (d), 127.3 (d), 127.8 (s), 128.6 (d), 129.6 (d), 138.3 (s), 138.8 (s), 140.8 (d), 149.1 (s), 150.6 (s), 166.1 (s).

Example 2

Evaluation of the Umami Effect of the Compound According to the Invention (in Water)

a) Pure Amide in Pure Water

The amides were evaluated at 20 ppm in mineral water in comparison with 0.05% monosodium glutamate (MSG). The trained panelists (5-10) were giving an umami taste intensity note. The Relative umami intensity (RUI) was calculated as follows:

RUI=(umami intensity of the amide)/(umami intensity of MSG)*10

The following table gives the average of the notes obtained from all panelists.

| Amide N° | | | | | | |
|---|---|---|---|---|---|---|
| 1 | 2 | 3 | 4 | 5 | 6 | 7 |
| RUI 5.6 | 3.8 | 3.3 | 10.2 | 3.2 | 3.7 | 9.8 |
| 8 | 9 | 10 | 11 | 12 | 14 | 17 |
| RUI 9.9 | 6.5 | 11.5 | 13.3 | 5.9 | 3.8 | 12.1 | b) In the Presence of Maltodextrin and MSG

Amides 1, 3, 4 and 8 were blended and diluted in maltodextrin at 10% w/w. Each blend was then added into a water solution containing MSG at 500 ppm in order to achieve a concentration ranging between 20 and 100 ppm of the amides, as indicated in the tables below:

|        | Sol 1 | Sol 2 | Sol 3 | Sol 4 | Sol 5 | Sol 6 | Sol 7 |
|--------|-------|-------|-------|-------|-------|-------|-------|
| MSG    | 500   | 500   | 500   | 500   | 500   | 500   | 500   |
| Amide 1| —     | —     | —     | —     | 20    | —     | —     |
| Amide 3| —     | 20    | 35    | 50    | —     | —     | —     |
| Amide 4| —     | —     | —     | —     | —     | 20    | —     |
| Amide 8| —     | —     | —     | —     | —     | —     | 20    | and also:

|         | Sol 8 | Sol 9 | Sol 10 | Sol 11 | Sol 12 | Sol 13 |
|---------|-------|-------|--------|--------|--------|--------|
| MSG     | 500   | 500   | 500    | 500    | 500    | 500    |
| Amide 7 | 20    | —     | —      | —      | —      | —      |
| Amide 9 | —     | 20    | —      | —      | —      | —      |
| Amide 10| —     | —     | 20     | —      | —      | —      |
| Amide 11| —     | —     | —      | 20     | —      | —      |
| Amide 12| —     | —     | —      | —      | 20     | —      |
| Amide 17| —     | —     | —      | —      | —      | 20     |

Sol = solution

A panel consisted in 15 to 20 trained panelists evaluating the samples for taste properties on a scale of −5 to 5 (−5 denoted no umami effect and 5 denoted extremely strong umami effect, 0 being the umami intensity of a reference umami solution containing
Monosodium Glutamate at 0.05%).
The samples were evaluated with and without nose clip to focus on taste.

Example 3

Evaluation of the Umami Effect of the Compound According to the Invention (in Applications)

1) Evaluation of Amides 1 and 3 in a Beef Bouillon

A beef stock was prepared containing the following ingredients:

| Ingredients in % w/w | |
|---|---|
| Maltodextrin | 52 |
| Onion Powder | 1.5 |
| Salt | 32.7 |
| White pepper | 0.1 |
| Yeast extract | 3.8 |
| Palm Oil | 7.6 |
| Caramel Color | 0.7 |
| Beef flavor | 1.5 |

10 g of beef stock was poured in 500 ml of boiling water. MSG and amides 1 and 3 were added to the beef bouillon at the dosages indicated in Table 1.

TABLE 1

| Ingredients in ppm | | | | |
|---|---|---|---|---|
|  | Bouillon 1 | Bouillon 2 | Bouillon 3 | Bouillon 4 |
| MSG | — | 700 | — | — |
| Amide 1 | — | — | — | 25 |
| Amide 3 | — | — | 50 | — |

The bouillons were presented to 5 trained panelists on a blind test basis. They were asked to rate the samples for taste properties on a scale of 0 to 10 (0 denoted no umami effect and 10 denoted extremely strong umami effect). The results are reported herein below:

|  | Umami intensity with nose-clip | Umami intensity without nose-clip | Description With nose-clip/without nose-clip |
|---|---|---|---|
| Solution 1 | 0 | 0 | Umami |
| Solution 2 | 0.91 | 0.76 | Umami, mouthfeel, salivating/nutty, woody |
| Solution 3 | 0.46 | 0.65 | Umami, mouthfeel, salty/nutty, woody |
| Solution 4 | 0.95 | 0.95 | Umami, salty, mouthfeel, salivating, astringent, metallic/nutty, earthy |
| Solution 5 | 1.13 | 1.25 | Umami, salty, sweet, mouthfeel, fatty |
| Solution 6 | 1.72 | 1.71 | Umami, mouthfeel, salty, sweet/nutty |
| Solution 7 | 1.25 | 1.46 | Umami, salty, mouthfeel, salivating, hot, cooling |
| Solution 8 | 1.27 | 1.34 | Umami, sweet, salty, astringent, bitter, mouthfeel |
| Solution 9 | 0.98 | 1.16 | Umami, sweet |
| Solution 10 | 0.88 | 0.94 | Umami, sweet, salty, pungent, bitter |
| Solution 11 | 0.8 | 0.95 | Umami, green, herbal, salivating |
| Solution 12 | 0.95 | 1.13 | Umami, salty, sweet, herbal, astringent, metallic |
| Solution 13 | 1.57 | 1.47 | Umami, salty, pungent, mouthfeel., herbal |

TABLE 2

Averages for each bouillon and descriptors

| | Umami intensity | Comments |
|---|---|---|
| Bouillon 1 | 2.1 | Yeasty, oniony, beef fat, flat |
| Bouillon 2 | 5.1 | More salty, round, umami, oniony, juicy, fatty |
| Bouillon 3 | 3.1 | Mouthfeel, salty, body |
| Bouillon 4 | 3.9 | Umami, round |

2) Evaluation of Amide 1 in a Chicken Bouillon

A chicken stock was prepared containing the following ingredients:

| | Ingredients in % w/w |
|---|---|
| Chicken meat powder | 2.5 |
| Maltodextrin | 32.2 |
| Garlic powder | 0.5 |
| Palm oil | 5 |
| Ground white pepper | 0.3 |
| Yeast extract | 10 |
| Onion powder | 3.25 |
| Toasted onion powder | 2 |
| Turmeric | 0.25 |
| Salt | 35 |
| Chicken fat | 5 |
| Chicken flavor | 4 |

10 g of chicken stock was poured in 500 ml of boiling water. MSG and amide 1 were added to the chicken bouillon at the dosages indicated in Table 3.

TABLE 3

| | Ingredients in ppm | | |
|---|---|---|---|
| | Bouillon 1 | Bouillon 2 | Bouillon 3 |
| MSG | — | 500 | — |
| Amide 1 | — | — | 20 |

The bouillons were presented to 5 trained panelists on a blind test basis as described above. The results are reported herein below:

TABLE 4

Averages for each bouillon and descriptors

| | Umami intensity | Comments |
|---|---|---|
| Bouillon 1 | 3.5 | Flat, salty |
| Bouillon 2 | 6.4 | Umami, mouthfeel, sweet, pleasant |
| Bouillon 3 | 6.3 | Umami |

3) Evaluation of Amides 1 and 4 in a Pork Flavor

Amides 1 and 4 were evaluated at 20 ppm by 5 trained panelists in a pork flavor on a blind test basis as described above. The results are reported herein below:

TABLE 5

Averages for each bouillon and descriptors

| | Umami intensity | Comments |
|---|---|---|
| Pork flavor | 4.5 | Meaty, pork, animalic, fatty, mouthfeel, balanced, good |

TABLE 5-continued

Averages for each bouillon and descriptors

| | Umami intensity | Comments |
|---|---|---|
| Pork flavor + Amide 1 | 6 | More umami, more meaty, pork notes enhanced, liquorice note, slightly cooling, fatty |
| Pork flavor + Amide 4 | 7 | More umami, rich strong meaty and pork notes, fatty |

4) Evaluation of Amides 1, 4, 8, 11, 12 in a chicken bouillon containing MSG and ribotides A chicken bouillon was prepared containing the following ingredients:

| | Ingredients in % w/w |
|---|---|
| Salt | 27 |
| MSG | 10 |
| Ribotides | 0.03 |
| Sugar | 4 |
| Vegetable oil | 2 |
| Chicken fat | 2 |
| White pepper powder | 0.1 |
| Yeast powder | 1.5 |
| Soy sauce powder | 0.5 |
| Chicken powder | 4 |
| Maltodextrin | 35.77 |
| Corn starch | 5 |
| Wheat powder | 3 |
| Egg powder | 4 |
| Chicken flavor | 1.1 |

1 g of chicken bouillon was poured into 100 ml of boiling water. Amides 1, 4, 8, 11, 12 were added to the chicken bouillon at the dosages indicated in Table 6:

TABLE 6

| | Ingredients in ppm | | | | | |
|---|---|---|---|---|---|---|
| | Bouillon | | | | | |
| | 1 | 2 | 3 | 4 | 5 | 6 |
| Amide 1 | — | 25 | — | — | — | — |
| Amide 4 | — | — | 25 | — | — | — |
| Amide 8 | — | — | — | 8 | — | — |
| Amide 11 | — | — | — | — | 5 | — |
| Amide 12 | — | — | — | — | — | 25 |

The bouillons were presented to 5 trained panelists on a blind test basis as described above. The results are reported herein below:

TABLE 7

Averages for each bouillon and descriptors

| | Umami intensity | Comments |
|---|---|---|
| Bouillon 1 | 5.3 | White meat, round, no off notes |
| Bouillon 2 | 6.3 | Sweet, meaty, balanced, very round, full |
| Bouillon 3 | 6.3 | Slow build, mouthfeel, sweet, umami, no off note, round, very balanced |
| Bouillon 4 | 6.7 | Strong umami, sweet, lingering, sweet and umami |
| Bouillon 5 | 6.7 | White meat, slightly astringent, very full, round, lasting, no off notes |
| Bouillon 6 | 6 | Mouthfeel, no off note, umami, sweet, very balanced slightly astringent |

5) Evaluation of amides 1 and 3 in marinated chicken

A marinade was prepared containing the following ingredients:

| | Ingredients in % w/w |
|---|---|
| Water | 90 |
| Salt | 4 |
| Hamine phosphate | 1 |
| Chicken White Meat Flavor | 5 |

MSG, amides 1 and 3 were added to the marinade at the dosages indicated herein below:

| | Ingredients in % w/w | | | |
|---|---|---|---|---|
| | Marinade 1 | Marinade 2 | Marinade 3 | Marinade 4 |
| Marinade | 100 | 100 | 100 | 100 |
| MSG | — | 0.3 | — | — |
| Amide 1 | — | — | 0.05 | — |
| Amide 3 | — | — | — | 0.05 |

Marinades were added with chicken meat in plastic bags in the following quantities:

| | Ingredients in % w/w | | | |
|---|---|---|---|---|
| | Marinated chicken 1 | Marinated chicken 2 | Marinated chicken 3 | Marinated chicken 4 |
| Chicken meat | 90 | 90 | 90 | 90 |
| Marinade 1 | 10 | — | — | — |
| Marinade 2 | — | 10 | — | — |
| Marinade 3 | — | — | 10 | — |
| Marinade 4 | — | — | — | 10 |

Samples were tumbled under vacuum for 25 minutes, and then cooked in a steam oven until meat temperature reaches 75° C. Samples were then frozen and reheat for 20 minutes at 80° C. in the oven before evaluation.

The marinated chicken samples were presented to 5 trained panelists on a blind test basis as described above. The results are reported herein below:

TABLE 8

Averages for each marinated chicken and descriptors

| | Umami intensity | Comments |
|---|---|---|
| Marinated chicken 1 | 1.3 | dry |
| Marinated chicken 2 | 4 | Strong, clean, pleasant aftertaste, juicy |
| Marinated chicken 3 | 4.9 | Very similar to MSG, meaty, round, brothy, balanced, sweet, full |
| Marinated chicken 4 | 3 | Clean, pleasant, strong impact, enhances chicken juicy, sweet |

6) Evaluation of Amides 1 and 3 in Surimi

Surimi was prepared using the following ingredients in % w/w:

| | Ingredients in % w/w |
|---|---|
| Frozen surimi base | 39.8 |
| Salt | 1.19 |
| Native Wheat Starch | 4.98 |
| Potato Starch | 4.98 |
| Sunflower Oil | 4.98 |
| Egg White | 6.97 |
| Ice | 36.6 |
| Crab extract | 0.5 |

The dry ingredients (salt, starches) were first put in a bowl chopper. The ice mix was added until homogenous. The surimi base was then added and mixed for 3 minutes. The oil was added while mixing, followed by the egg white.

MSG and the amides 1 and 3 were added to the surimi preparation at the dosages indicated herein below:

| | Surimi 1 | Surimi 2 | Surimi 3 | Surimi 4 |
|---|---|---|---|---|
| MSG | — | 5000 ppm | — | — |
| Amide 1 | — | — | 50 ppm | — |
| Amide 3 | — | — | — | 50 ppm |

The 4 surimis were put in cooking bags and cooked for 45 minutes in a steam oven at 90° C. The samples were then quickly cooled down.

The surimi samples were presented to 5 trained panelists on a blind test basis as described above. The results are reported herein below:

TABLE 9

Averages for each surimi and descriptors

| | Umami intensity | Comments |
|---|---|---|
| Surimi 1 | 2.2 | Flat, eggy, slightly amine, not really fishy |
| Surimi 2 | 5.3 | Sweet, umami, round, sweet, salty |
| Surimi 3 | 3.2 | Slightly sweet, umami, juicy, round, fishy, crab |
| Surimi 4 | 3.7 | Crab, slightly amine, sweet, fishy, oyster, crab, juicy |

What is claimed is:

1. A method of enhancing an umami taste of a flavored article, the method comprising introducing to the flavored article a compound of formula (II)

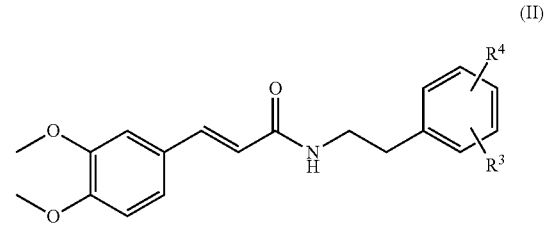

wherein:
 $R^3$ is a hydrogen atom or a $C_1$ to $C_5$ alkyl group,
 $R^4$ is a $C_1$ to $C_5$ alkyl group or an $OR^6$ group, and
 $R^6$ is a $C_1$ to $C_5$ alkyl group;
wherein the compound of formula (II) is introduced to the flavored article at a concentration ranging from 0.5 ppm to 300 ppm.

2. The method of claim 1, wherein the flavored article comprises a flavor carrier or a foodstuff base.

3. The method of claim 1, wherein the flavored article comprises an umami-imparting ingredient.

4. The method of claim 3, wherein the umami-imparting ingredient is monosodium glutamate (MSG), a ribotide, inosine monophosphate, guanosine monophosphate, or any combination thereof.

5. The method of claim 2, wherein the flavored article comprises a foodstuff base.

6. The method of claim 5, wherein the foodstuff base is a seasoning, a condiment, a meat-based product, a soup, a carbohydrate-based product, a dairy product, a fat product, a savory product, an imitation product, a pet food, or an animal food.

7. The method of claim 1, wherein the flavored article is a stock, a savory cube, a powder mix, a flavored oil, a sauce, a salad dressing, a mayonnaise, a poultry product, a beef product, a pork based product, a seafood product, a surimi product, a fish product, a clear soup, a cream soup, a chicken soup, a beef soup, a tomato soup, an asparagus soup, instant noodles, rice, pasta, potato flakes, fried noodles, pizza, tortillas, wraps, a spread, a cheese, a regular margarine, a low fat margarine, a butter/margarine blend, a butter, a peanut butter, a shortening, a processed cheese, a flavored cheese, a snack, a biscuit, an egg product, a potato chip, a tortilla chip, a microwave popcorn, nuts, a bretzel, a rice cake, a rice cracker, a cheese made from oils, fats, thickeners, a vegetarian meat replacer, or a vegetarian burger.

8. The method of claim 1, wherein: $R^3$ is a hydrogen atom or a $C_{1-3}$ alkyl group; $R^4$ is a $C_{1-3}$ alkyl group or an $OR^6$ group; and $R^6$ is a $C_1$ to $C_3$ alkyl group.

9. The method of claim 1, wherein the compound of formula (II) is:
- (E)-3-(3,4-dimethoxyphenyl)-N-(4-methoxyphenethyl) acrylamide;
- (E)-3-(3,4-dimethoxyphenyl)-N-(3-methoxyphenethyl) acrylamide;
- (E)-3-(3,4-dimethoxyphenyl)-N-(3-ethoxyphenethyl) acrylamide;
- (E)-3-(3,4-dimethoxyphenyl)-N-(3-propoxyphenethyl) acrylamide;
- (E)-3-(3,4-dimethoxyphenyl)-N-(4-isopropoxy-phenethyl)acrylamide;
- (E)-3-(3,4-dimethoxyphenyl)-N-(4-ethylphenethyl)acrylamide;
- (E)-3-(3,4-dimethoxyphenyl)-N-(3,4-dimethylphenethyl) acrylamide;
- (E)-3-(3,4-dimethoxyphenyl)-N-(4-isopropylphenethyl) acrylamide; or
- (E)-3-(3,4-dimethoxyphenyl)-N-(3-methylphenethyl) acrylamide.

\* \* \* \* \*